United States Patent
Huang et al.

(10) Patent No.: US 9,895,345 B2
(45) Date of Patent: Feb. 20, 2018

(54) USE OF LAPPAOL F TO INHIBIT TUMOR CELL GROWTH

(71) Applicants: The Research Foundation Foundation for the State University of New York, Syracuse, NY (US); Guangzhou University of Chinese Medicine, Guangzhou (CN)

(72) Inventors: Ying Huang, Manlius, NY (US); Yingjie Hu, Guangzhou (CN); Qing Sun, Acton, MA (US); Kanglun Liu, Guangzhou (CN); Xiaoling Shen, Guangzhou (CN); M. Saeed Sheikh, Manlius, NY (US)

(73) Assignees: The Research Foundation for the State University of New York, Syracuse, NY (US); Guangzhou University of Chinese Medicine, Guangzhou (CN)

( * ) Notice: Subject to any disclaimer, the term of this patent is extended or adjusted under 35 U.S.C. 154(b) by 0 days.

(21) Appl. No.: 14/889,534

(22) PCT Filed: May 6, 2014

(86) PCT No.: PCT/US2014/036898
§ 371 (c)(1),
(2) Date: Nov. 6, 2015

(87) PCT Pub. No.: WO2014/182653
PCT Pub. Date: Nov. 13, 2014

(65) Prior Publication Data
US 2016/0367524 A1    Dec. 22, 2016

Related U.S. Application Data

(60) Provisional application No. 61/820,542, filed on May 7, 2013.

(51) Int. Cl.
*A61K 31/365* (2006.01)
*A61K 45/06* (2006.01)

(52) U.S. Cl.
CPC ............ *A61K 31/365* (2013.01); *A61K 45/06* (2013.01)

(58) Field of Classification Search
CPC .................................................. A61K 31/365
See application file for complete search history.

(56) References Cited

U.S. PATENT DOCUMENTS

2006/0276527 A1    12/2006    Tidmarsh
2007/0166255 A1    7/2007    Gupta

FOREIGN PATENT DOCUMENTS

CN    102070685 A    5/2011
KR    20080107794    12/2008

OTHER PUBLICATIONS

Ming et al. Pharmaceutical Biology, 2004, vol. 42, No. 1, pp. 44-48.*
Grunbaum et al. Can. J. Urol., 2005, vol. 12, No. 5, pp. 2841-2842 (Abstract Attached).*
Whibley et al. Nature Reviews, Feb. 2009, vol. 9, pp. 95-107.*
Chan, Y., et al., A review of the pharmacological effects of *Arctium lappa* (burdock), Inflammopharmacol, Oct. 28, 2010, vol. 19, pp. 245-254.
Machado, F.B., et al., Evaluation of the Antiproliferative Activity of the Leaves from Arctium lappa by a Bioassay-Guided Fractionation, Molecules, Feb. 14, 2012, vol. 17, pp. 1852-1859.
Sun, Q., et al., Lappaol F, a Novel Anticancer Agent Isolated from Plant *Arctium Lappa* L., Molecular Cancer Therapeutics, Nov. 12, 2013, vol. 13, No. 1, pp. 49-59.
Tezuka et al., Anti-austeric activity of phenolic constituents of seeds of arctium lappa, Natural Product Communications, vol. 8, No. 4, pp. 463-466. Jan. 1, 2013.
Umehara et al., Studies on differentiation inducers. VI. Lignan derivatives from arctium fructus, Chemical and Pharmaceutical Bulletin, vol. 44, No. 12, pp. 2300-2304. Dec. 1, 1996.
Park et al., Lignans from Arctium lappa and their inhibition of LPS-induced nitric oxide production, Chemical & Pharmaceutical Bulletin, vol. 55, No. 1, Jan. 2007, pp. 150-152. Jan. 1, 2007.
Zhang, X., et al., Research Progress on Anti-cancer Active Components and Action Mechanism of Arctii Fructus, Modern Chinese Medicine, Dec. 31, 2012, vol. 14, No. 12, pp. 12-17.

* cited by examiner

*Primary Examiner* — James D. Anderson
(74) *Attorney, Agent, or Firm* — Hodgson Russ LLP

(57) ABSTRACT

Provided is a method for inhibiting the growth of tumor cells comprising administering to an individual in need of treatment, a composition comprising a therapeutically effective amount of Lappaol F. Also provided are compositions comprising Lappaol F and a pharmaceutically acceptable carrier.

14 Claims, 13 Drawing Sheets

SEQUENCE LISTING

<160> NUMBER OF SEQ ID NOS: 2

<210> SEQ ID NO 1
<211> LENGTH: 21
<212> TYPE: DNA
<213> ORGANISM: artificial sequence
<220> FEATURE:
<223> OTHER INFORMATION: targeting sequence -continued

```
<400> SEQUENCE: 1
cgctctacat cttctgcctt a                                             21

<210> SEQ ID NO 2
<211> LENGTH: 21
<212> TYPE: DNA
<213> ORGANISM: artificial sequence
<220> FEATURE:
<223> OTHER INFORMATION: targeting sequence

<400> SEQUENCE: 2
gagcgatgga acttcgactt t                                             21
```

USE OF LAPPAOL F TO INHIBIT TUMOR CELL GROWTH

CROSS REFERENCE TO RELATED APPLICATIONS

This application claims priority to U.S. Provisional application No. 61/820,542, filed on May 7, 2013, the disclosure of which is incorporated herein by reference.

BACKGROUND OF THE INVENTION

Cancer continues to be a major health problem in the United States and world-wide. In the United States, more than 1.5 million estimated new cancer cases were diagnosed in 2012 and 577,190 of cancer patients died due to cancer. Cancer-caused deaths account for nearly ¼ of all deaths in the US. Although enhanced early-stage tumor diagnosis and management have significantly increased patient survival, development and discovery of new anticancer therapies are still needed because some patients exhibit insensitivity to current anticancer drugs or develop drug-resistance after a period of treatment.

SUMMARY OF THE INVENTION

This disclosure provides methods and compositions for inhibiting the growth of tumor cells. As used herein, the terms tumor cells and cancer cells are used interchangeably. In one embodiment, the tumor cells are solid tumor cells. In another embodiment, the tumor cells are blood cancer cells (blood tumor cells). In one aspect, the composition comprises Lappaol F in a pharmaceutically acceptable carrier. In one aspect, the method comprises administering to an individual a composition comprising a therapeutically effective amount of Lappaol F.

*P<0.05, compared with Lappaol F group. Photography displayed in B shows the actual tumors extracted from the mice untreated (vehicle, N=7) or treated with Lappaol F (5 mg/kg, N=7; and 10 mg/kg, N=6).

DETAILED DESCRIPTION OF THE INVENTION

We have identified an anti-tumor (anti-cancer) cell proliferation effect of Lappaol F and demonstrated its cell growth inhibitory activity in tumor cell lines and tumor inhibitory activity in an animal model. Our results indicate that, Lappaol F exerts a strong growth inhibition on a variety of tumor cell lines representing different tissues, including colon, breast, lung, cervix, prostate and leukemia, melanoma and sarcoma cells.

In one embodiment, this disclosure provides compositions and methods for inhibiting the growth of cancer cells. The compositions comprise Lappaol F. The method comprises administering to an individual a therapeutically effective amount of a composition comprising Lappaol F. The structure of Lappaol F is known. It is also provided in FIG. 1A.

In one embodiment, this invention provides a method for inhibiting the growth of solid tumor cells comprising administering to an individual a therapeutically effective amount of a composition comprising Lappaol F. In another embodiment, this invention provides a method for inhibiting the grown of blood tumor (blood cancer) cells, including leukemia, lymphoma and myeloma comprising administering to an individual a therapeutically effective amount of a composition comprising Lappaol F.

Figure 3:
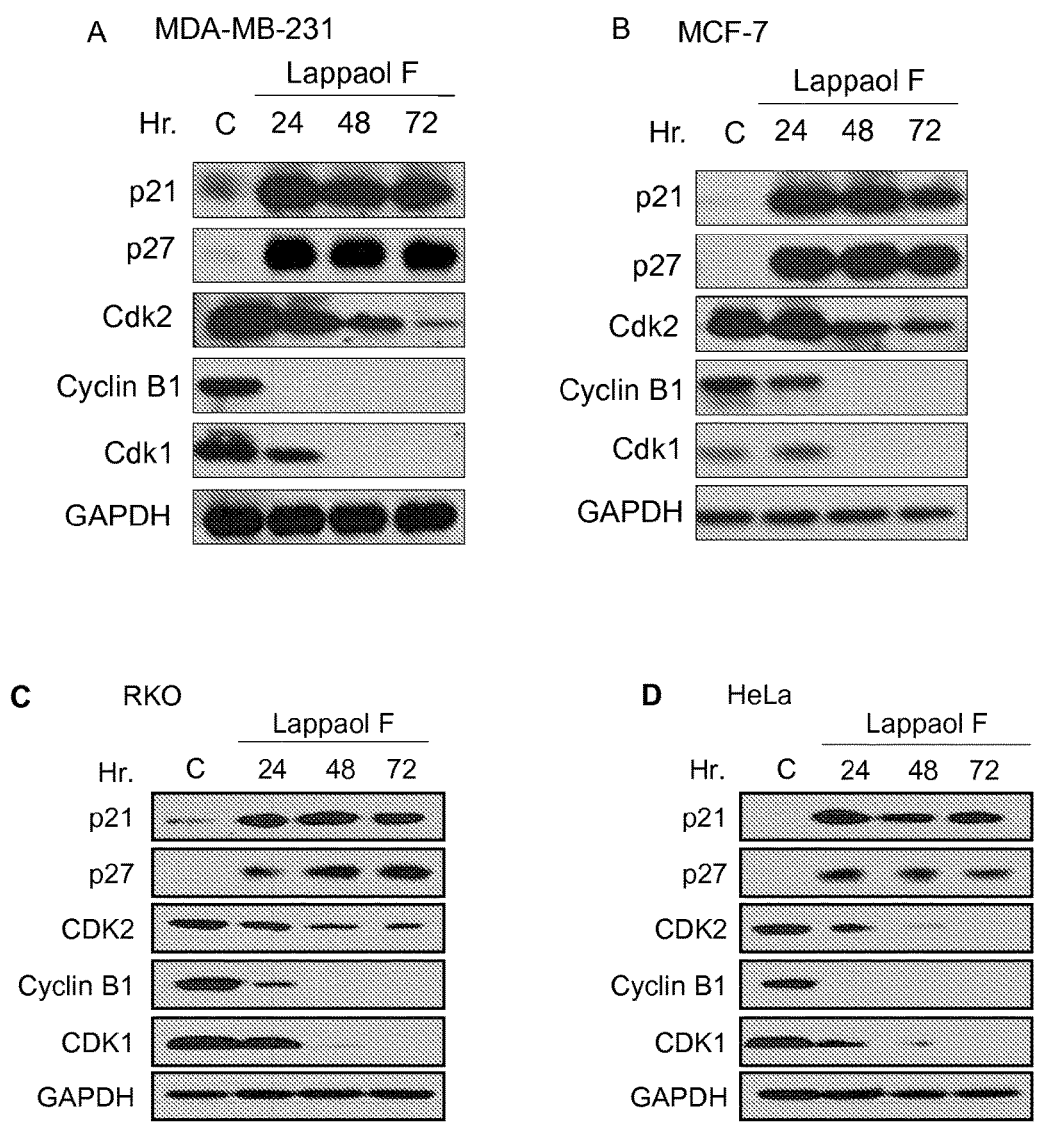
FIG. 3: Regulation of key cell cycle regulatory proteins by Lappaol F. A-D. The indicated cells were treated with vehicle (DMSO) or Lappaol F (50 µM) for indicated time and protein expression of different cell cycle regulatory protein was analyzed by Western blotting. "C": vehicle-treated control.
Figure 5:
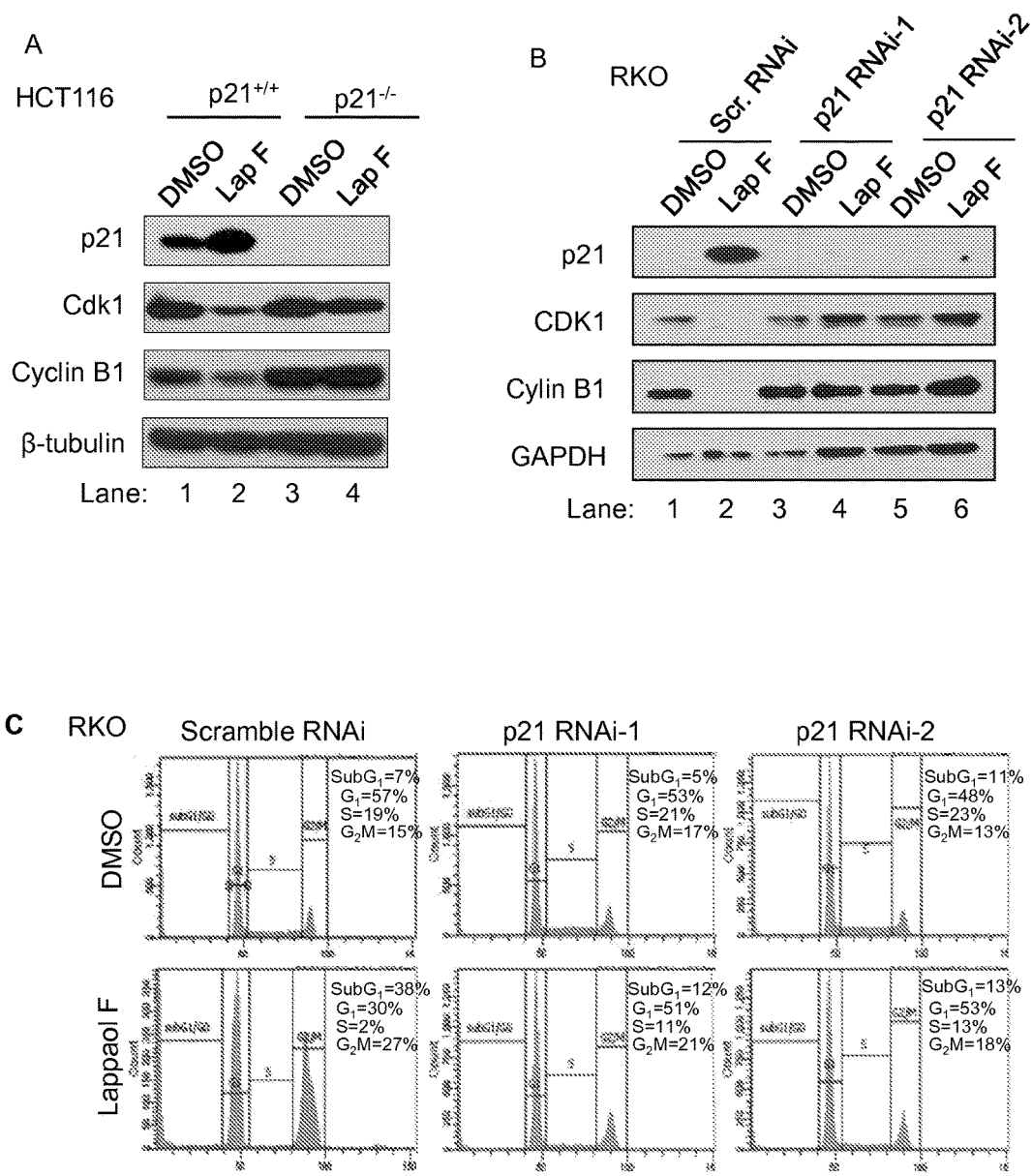
FIG. 5: Role of p21 in Lappaol F-mediated cyclin B/CDK1 down-regulation and $G_2$ arrest. (A & B) Cyclin B and CDK1 protein expression was analyzed on Lappaol F untreated (DMSO) or treated (Lap F) p21-proficient (parental) and -deficient (p21 gene deletion) HCT116 cells (A); or in cells expressing the scramble shRNA or the p21-specifc shRNAs that targeted two different regions of the p21 transcript (B). C & D. Cell cycle analyses of RKO and MDA-MB-231 cells expressing scramble shRNAi or two different p21 shRNAs. Cells were untreated (DMSO) or treated with Lappaol F (25 µM) for 72 hrs and cell cycle profile was determined by the flow cytometry.
Figure 5:
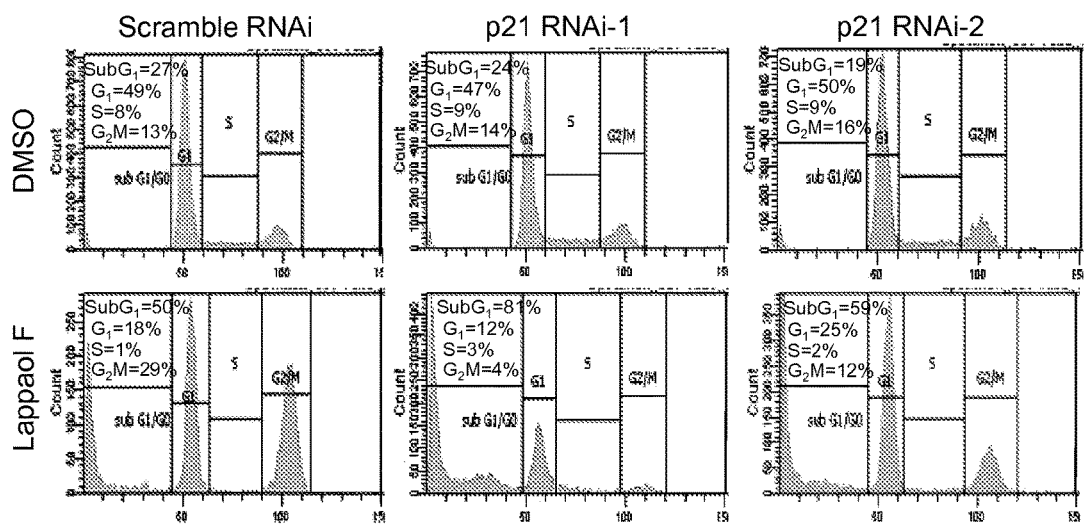

While not intending to be bound by any particular theory, our studies indicate that Lappaol F mediates its growth suppression effect predominantly through inducing $G_1$ and $G_2$ cell cycle arrest. In addition to its effect on cell cycle regulation, Lappaol F also triggers cell death in some tumor cell lines. The cell cycle profile of the different cell lines responding to Lappaol F treatment is not the same. For instance, MCF-7 cells were predominantly arrested at $G_1$ while RKO and MDA-MB-231 cells were mainly arrested at $G_2$. Lappaol F modulated the expression of a number of key cell cycle regulators such as p21, p27, cyclin B and CDK1 and CDK2 (FIG. 3). Lappaol F-induced induction of p21 and p27 and suppression of CDK1 may be sufficient to prevent cell cycle progression from $G_1$ to S. Similarly, strong suppression of CDK1 and cyclin B may be sufficient to arrest cells at $G_2$, Our studies further identify that p21 is critical for Lappaol F-mediated cyclin B and CDK1 downregulation and $G_2$-arrest. Lappaol F-mediated cyclin B and CDK1 reduction was abolished in p21-depleted cells (FIG. 5), and furthermore, Lappaol F-mediated $G_2$ cell cycle arrest was also significantly altered in the absence of p21 (FIG. 5). Thus, our results suggest that p21 induction is an important event in Lappaol F-mediated cellular responses and plays a key role in Lappaol F-mediated cyclin B/CDK1 suppression and $G_2$ cell cycle arrest.

Figure 6:
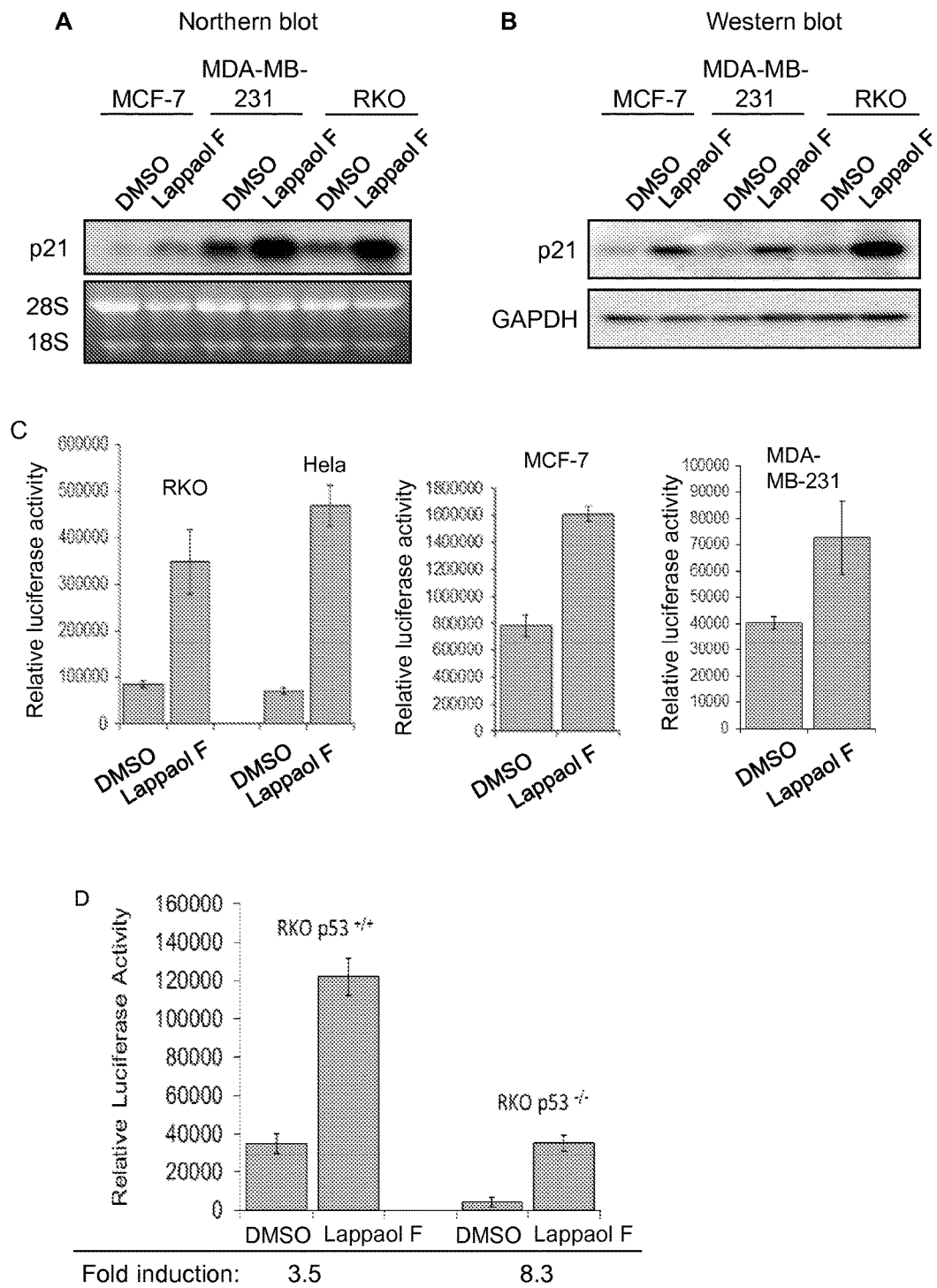
FIG. 6: Lappaol F induces p21-promoter activation in cells with wild-type p53 and defective-p53. A&B MCF-7, MDA-MB-231 and RKO cells were untreated (DMSO) or treated with Lappaol F (50 µM) for 48 hrs; cells were then split into two parts; one part was used to analyze p21 mRNA expression by Northern blotting (A) and another part was utilized for p21 protein analysis by Western blotting (B). A full-length p21 cDNA was used as a probe for Northern blot analysis. C & D. p21 promoter luciferase activity in Lappaol F-treated and untreated cells with different p53 status. RKO and MCF-7 cells express the wild type-p53 protein whereas MDA-MB-231 expressing the mutant-p53. Hela cells harbor human papilloma virus; and p53 protein is not functional in these cells. Cells, transfected with p21 promoter luciferase construct, were untreated (DMSO) or treated with Lappaol F (50 µM) for 24 hours then analyzed for luciferase activity.

Our studies also demonstrate that Lappaol F induced strong induction of p21 mRNA expression which could indicate that the activation of p21 in response to Lappaol F occurs at the transcriptional level. The enhanced p21 mRNA expression by Lappaol F may occur due to increased p21 promoter activity (FIG. 6). It is noteworthy that p21 promoter activation after Lappaol F treatment occurred in cells expressing the wild-type p53 (RKO and MCF-7) as well as in cells harboring the mutant- and non-functional p53 (MDA-MB-231 and HeLa). Further, p21 can be induced in cell lacking the p53 gene (p53I). This indicates that Lappaol F-triggered induction of p21 occurs in a p53-independent manner.

Figure 7:
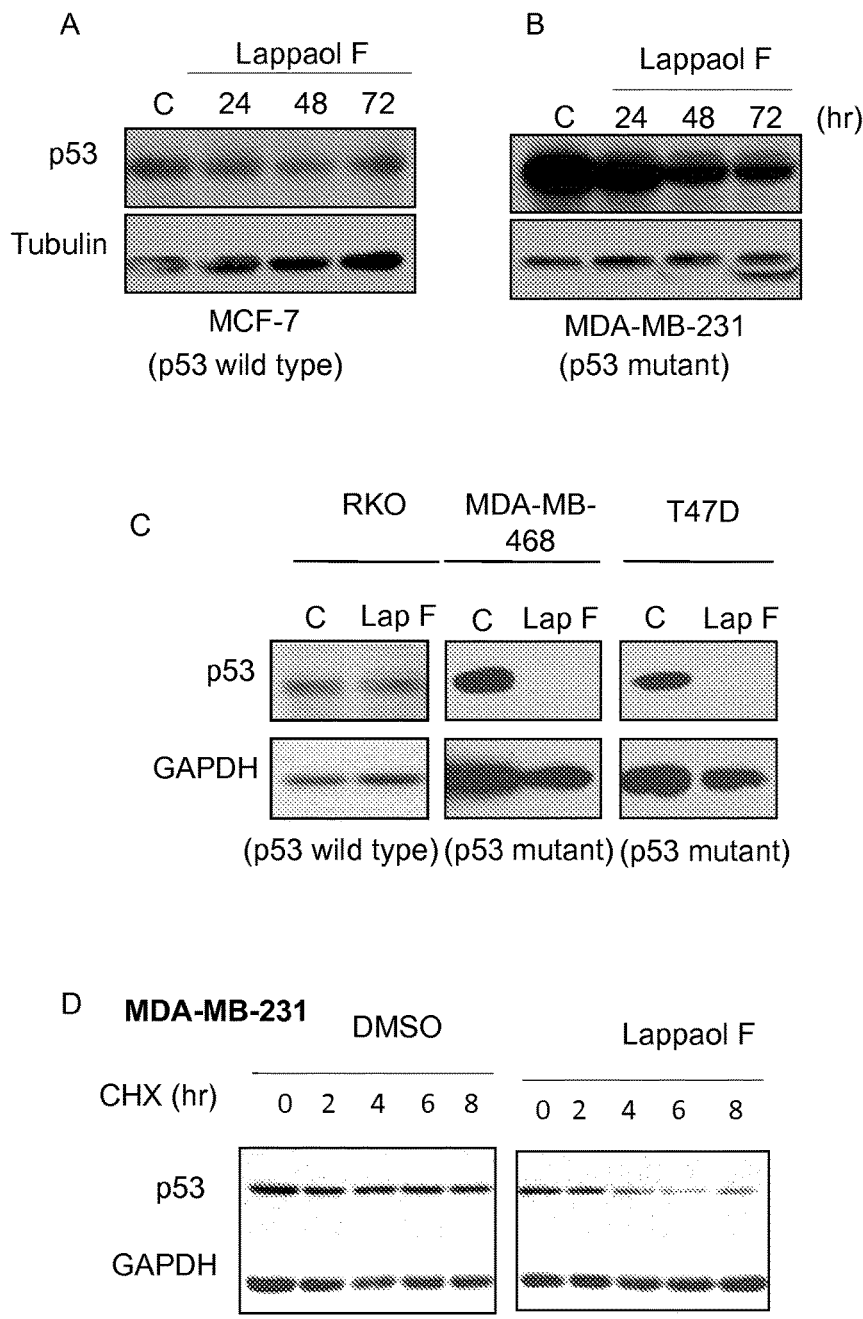
FIG. 7: Lappaol F suppresses expression of mutant-p53 by reducing its half-life. A-C. Lappaol F has minimal effect on wild-type p53 protein expression in cells (MCF-7 and RKO) expressing wild-type p53 (A & C); however, Lappaol F strongly reduces mutant-p53 protein expression in MDA-MB-231, MDA-MB-468 and T47D cells (B & C). D & E. Treatment of Lappaol F reduces mutant-p53 protein half-life in MDA-MB-231 cells. Cells were first treated with or without with Lappaol F (50 µM) for 24 hours, cycloheximide (50 µg/ml) was then added into the cell culture medium for 0-8 hours and cells were harvested at 0, 2, 4, 6 and 8 hours after cycloheximide was added. Samples were subjected to Western blot analysis and the half-life of mutant p53 for cells treated with or without Lappaol F was determined F & G. Lappaol F decreases mutant p53 protein half-life in T47D cells. Mutant-p53 half-life was determined as described.
Figure 7:
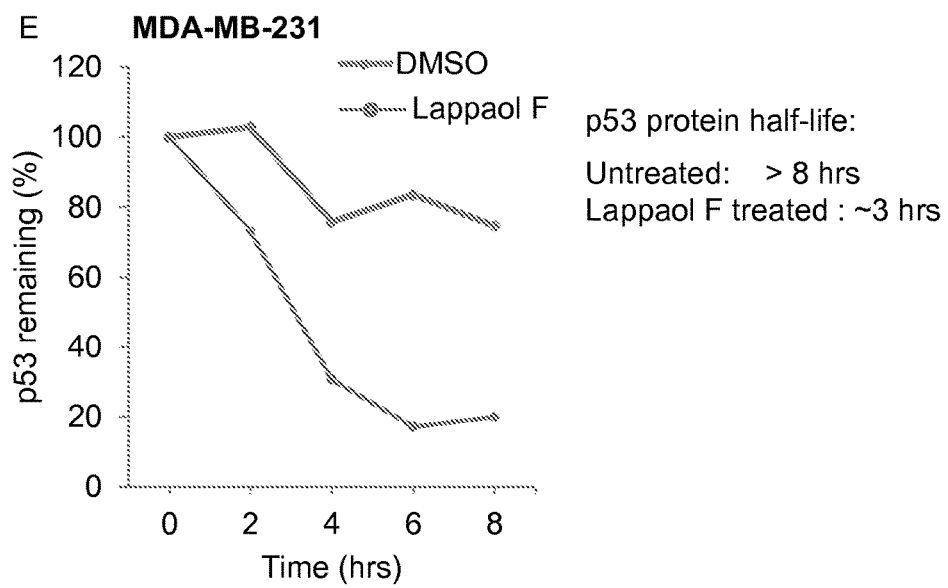
Figure 7:
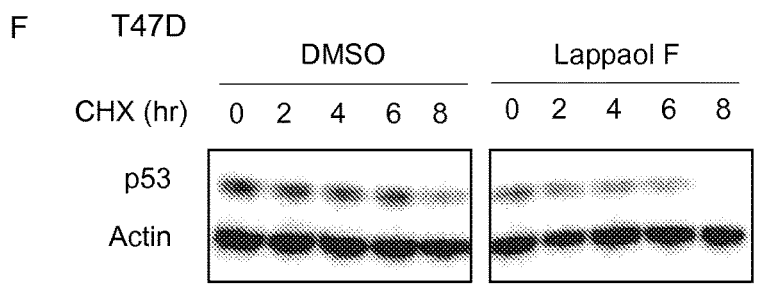
Figure 7:
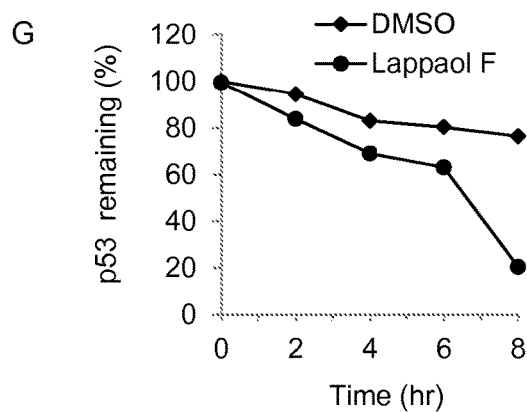

Phenotypically, Lappaol F also induced growth suppression in cells expressing wild-type-p53 (MCF-7 and RKO) or mutant/non-functional p53 (MDA-MB-231 and HeLa). Lappaol F also reduces mutant-p53 expression and decreases mutant-p53 protein half-life (FIG. 7). Our findings indicating that Lappaol F suppresses mutant-p53 expression and provides support for the use of Lappaol F in targeting tumor cells harboring mutant-p53.

Figure 8:
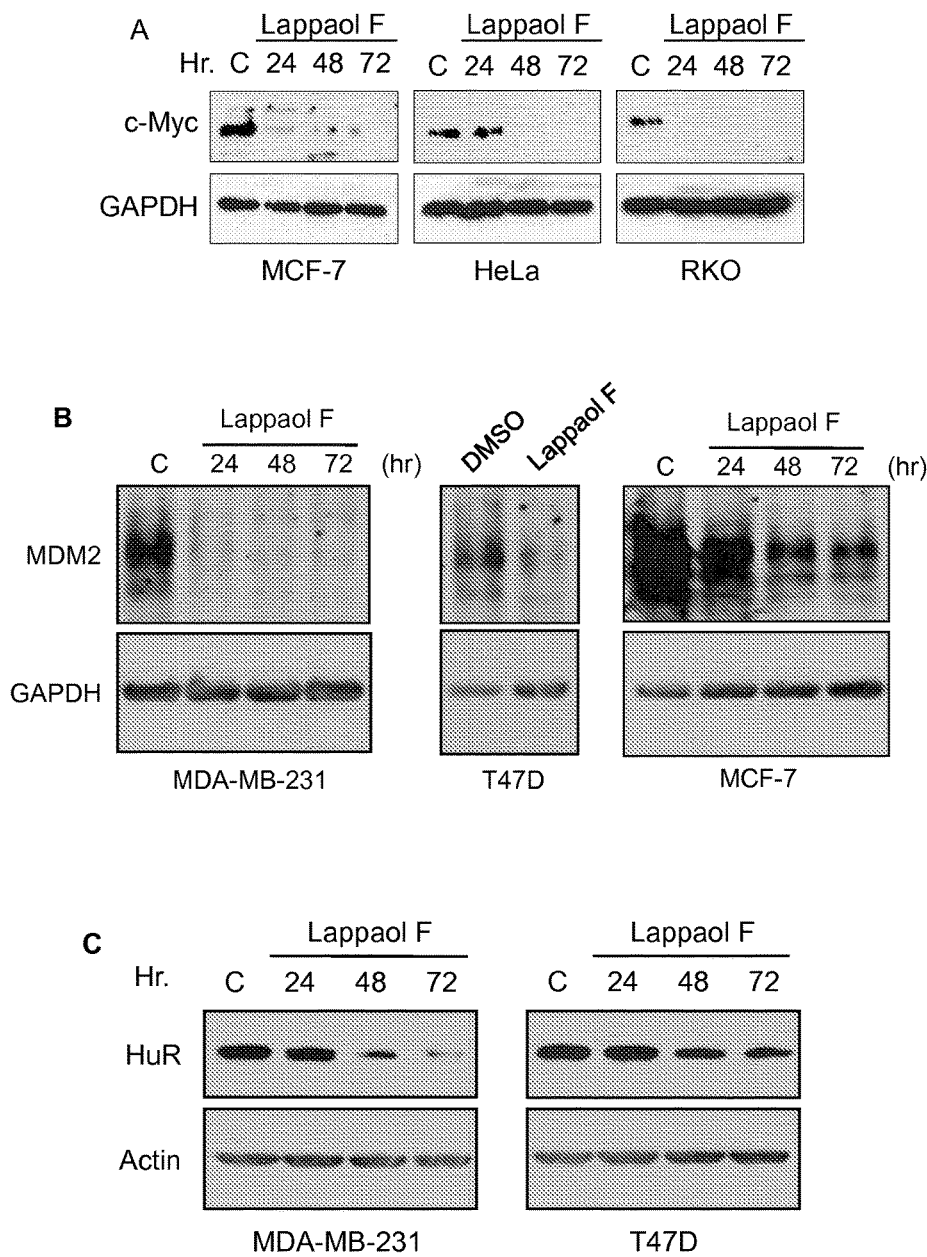
FIG. 8: Lappaol F down regulates the expression of several oncogenic proteins commonly overexpressed in human cancers and linked to oncogenic transformation. A-C. Lappaol F suppresses the expression of c-Myc (A), MDM2 (B) and HuR (C). Cells were untreated ("C") or treated with Lappaol F (50 µM) for the indicated times and Western blot analyses were performed using the indicated antibodies.

Our results also indicate that Lappaol F significantly suppresses the expression of a number of oncogenic proteins; these include c-Myc, MDM2 and HuR proteins (FIG. 8). All these indicated proteins (c-Myc, MDM2 and HuR) are commonly overexpressed in various human cancers and linked to oncogenic transformation and maintenance of oncogenic phenotypes in cancer cells. C-Myc, MDM2 are also important therapeutic targets for anticancer drug development. Out studies indicate that Lappaol F, by suppressing multiple oncogenic proteins, may effectively inhibit the growth of cancer cells overexpressing these oncgnenic proteins.

Figure 9:
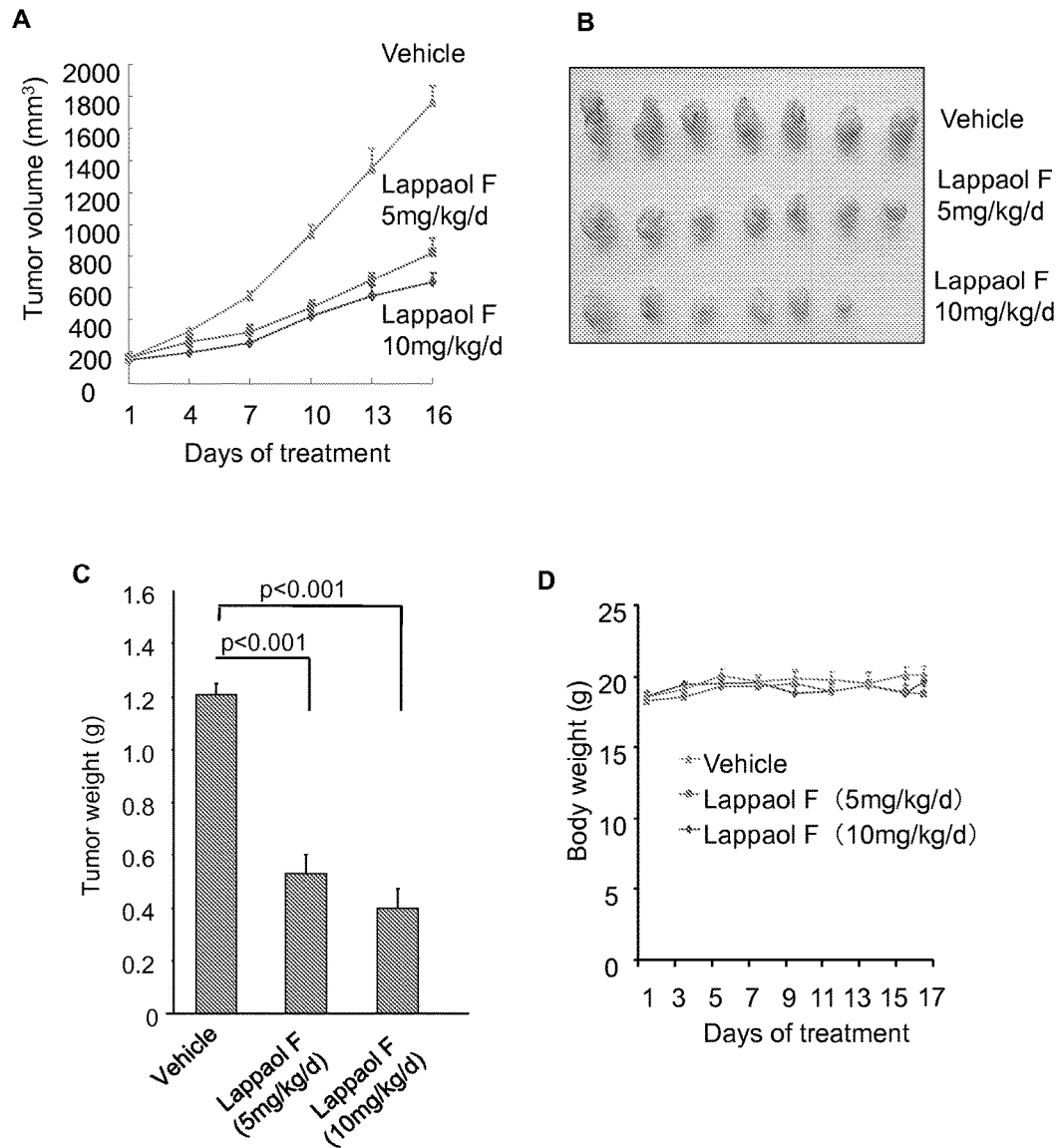
FIG. 9: The growth inhibitory effect of Lappaol F on HeLa tumor cells as xenografts. Tumor-bearing mice were treated with the vehicle or Lappaol F (5 mg/kg/day or 10 mg/kg/day) (i.v.) for 15 days. Tumor size, tumor volume and animal body weight were monitored as described in Materials and Methods. Results are expressed as means±SEM.

Lappaol F exerted strong growth inhibition on HeLa tumors grafted onto the nude mice (FIG. 9). It is known that HeLa cells harbor the human papilloma virus which disrupts the function of p53. Inactivation of p53 is a common feature of human cancer cells and many human cancers harbor the defective p53. Based on the knowledge gained from our study, Lappaol F can be used to inhibit the growth of tumor cells that have wild type p53 as well as mutant p53. As described in the example presented herein, we observed that given daily at a dose of 5 mg/kg/day or 10 mg/kg/day for 15 days significantly inhibited the growth of xenografted HeLa cell tumors by 54% (p<0.001) and 64% (p<0.001) as compared to the vehicle-treated cohorts. In addition, animals appeared to tolerate the treatment of Lappaol F without significant body weight changes during treatment.

Currently, there are a number of anticancer drugs in clinical use that target cell cycle regulation; for example, the *vinca* alkaloids (vincristine, vinblastine, vinorelbine and vindesine), the taxanes (paclitaxel or docetaxel) and colchicine. These drugs are derived from plants and also share a common mechanism of action which is to induce mitotic arrest. These drugs are considered to achieve this affect by altering microtubule polymerization potential and preventing normal mitotic spindle formation. Cancer cells can develop resistance to these chemotherapeutics via numbers of mechanisms including for example, alterations in microtubule dynamics; alterations in β- or α-tubulin isotype levels or compositions; mutations occurring in tubulins which affect drug binding; protein modifications that modulate tubulin/microtubule dynamic regulatory proteins. Such cellular changes are expected to alter the interplay between microtubules and microtubule-targeting drugs thereby giving rise to drug resistance. Our study has identified that Lappaol F functions to mainly arrest cell cycle progression at the $G_1$ and $G_2$ phases through regulation of cell cycle regulatory proteins. The mechanism of action of Lappaol F appears to be different from the above noted microtubule-targeting drugs. It is therefore, likely that the mechanisms that lead to drug resistance against the above noted microtubule-targeting drugs would not affect the action of Lappaol F. Thus, in one embodiment, Lappaol F could also be used in cases where the other anticancer drugs have failed. Alternatively, because their mechanisms of action are different, in one embodiment, the present composition may be used in combination with other anticancer agents such as Cisplatin, Doxorubicin, Etoposide, Bleomycin, Cetuximab and Trastuzumab. Such combination can be used to inhibit the growth of p53 wild-type as well as p53-defective tumors.

In one embodiment, this disclosure provides a method for inhibiting the growth of tumors. The method comprises administering to an individual who has been diagnosed with having a tumor, a composition comprising Lappaol F.

In one embodiment, Lappaol F can be provided in compositions such as pharmaceutical preparations. Compositions for use in therapeutic and/or prophylactic approaches can be prepared by mixing Lappaol F with any suitable pharmaceutically acceptable carriers, excipients and/or stabilizers. Some examples of compositions suitable for mixing with the agent can be found in: Remington: The Science and Practice of Pharmacy (2005) 21st Edition, Philadelphia, Pa. Lippincott Williams & Wilkins. It will be recognized by those of skill in the art that the form and character of the particular dosing regimen for any Lappaol F preparation employed in the method will be dictated at least in part by the route of administration and other well-known variables, taking into account such factors as the size, gender, health and age of the individual to be treated, and risk factors associated with cancer development for the individual, such as occupational, behavioral or family history related parameters. Based on such criteria, one skilled in the art can determine an effective amount to administer to the individual. In one embodiment, Lappaol F can be administered at a dose of 1 mg/kg/day to 10 mg/kg/day and all amounts therebetween to the tenth decimal point and all ranges therebetween. The dose (higher or lower than 10 mg/kg/day) and administration frequency can be adjusted as seen fit by a clinician. The administration may be carried out for a period ranging from 1 day to 30 days or longer as needed.

In our studies, it was surprisingly observed that intraperitoneal injection in animal containing HeLa xenografts did not show any significant effect while intravenous injection did. Because drug absorption after IP administration primarily goes through the portal circulation and the liver prior to reaching systemic circulation and tumor target site, our results showing that Lappaol F was not effective when administrated via the IP route could indicate that Lappaol F may be modified in the liver due to the first-pass metabolism. Therefore, compositions comprising Lappaol F can be administered to an individual using any suitable methods and routes that may bypass the first-pass metabolism, including parenteral, intratumoral, intrapulmonary, intranasal and intracranial injections. Parenteral infusions include intramuscular, intravenous, intraarterial, intraperitoneal, and subcutaneous administration. It is well within the purview of those skilled in the art to determine an appropriate route of administration for a particular tumor. In certain embodiments, the method can be performed prior to, concurrently, or subsequent to conventional anti-cancer therapies, including but not limited to chemotherapies, surgical interventions, and radiation therapy.

In one embodiment, a composition comprising Lappaol F can be administered to an individual diagnosed with having a tumor, which has not responded to another anticancer agent such as *vinca* alkaloids (vincristine, vinblastine, vinorelbine and vindesine), the taxanes (paclitaxel or docetaxel) and colchicine.

It is expected that there will be no particular limit to the type of tumor for which the present disclosure provides a therapeutic approach. In embodiments, the tumor is a solid tumor, or a blood tumor (such as leukemia, lymphoma or myeloma). Examples include but are not necessarily limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, thymoma, and Waldenstrom's macroglobulinemia. The tumors may exhibit wild type-p53 or may exhibit mutant-p53 or harbor virus (such as human papilloma virus) that disrupt the function of p53.

The following example described the invention further. It is intended to be illustrative and should not be construed to be limiting.

It is expected that the invention will be suitable for therapy of any cancer in individuals of all ages. In one embodiment, the individual is a mammal. The invention is expected to be suitable for human and veterinary purposes.

Our studies have also identified that Lappaol F suppresses the expression of a number of oncogenic proteins such as mutant-p53, c-Myc, MDM2 and HuR (FIGS. 7 & 8). Mutant-p53, c-Myc and MDM2 are the targets of anticancer therapeutics. Elevated expression of MDM2 and c-Myc are commonly observed in human cancers. Mutant-p53 status or overexpression of MDM2 and/or overexpression of c-Myc are important for oncogenic transformation and the maintenance of oncogenic phenotypes in cancer cells. Our results shown in FIGS. 7 & 8 indicate that Lappaol F is capable of inhibiting the expression of these oncogenic proteins, and such characteristics are important advantages of this novel anticancer agent. When multiple oncogenic proteins are concurrently targeted and inhibited, growth inhibition of the cancer cells is more likely to be achieved. Clinical studies have shown that the single-targeted anticancer drug often develops drug-resistance in patients after a period of administration of the drug. This occurs mostly due to alteration/mutation associated with single target. By simultaneously targeting multiple oncoproteins, Lappaol F could reduce the likelihood of development of drug resistance in cancer cells. In one embodiment, Lappaol F can be administered to an individual diagnosed with having a tumor which expresses mutant-p53 or overexpresses MDM2 and/or HuR and/or c-Myc oncogenic proteins.

The following example is provided to further illustrate the invention.

EXAMPLE

Materials and Methods

Cell Lines, Cell Culture Conditions and Reagents

Human cancer cell lines MCF-7, MDA-MB-231, MDA-MB-468, Hs578T (breast), RKO and HT29 (colon), A549 (lung, non-small cell), DU145 (prostate) and several other tumor cell lines include K562, HL60, Jurkat (leukemia), A375, Mo1103 (melanoma) and U20S (osteosarcoma) were maintained in Dulbecco's modified Eagle's medium supplemented with 10% fetal bovine serum (FBS) (Gemini Bio-Products, West Sacramento, Calif.). HCT116 colon cancer cells [p21-proficient ($p21^{+/+}$) or p21-deficient ($p21^{-/-}$) were grown in RPMI-1640 medium with 10% FBS. HeLa cervical cancer cells were grown in DMEM or RPMI-1640 medium with 10% FBS. Human non-tumorigenic breast epithelial MCF-10A cells were grown in Mammary Epithelial Cell Growth Medium with supplements provided in SingleQuots™ Kit (Lonza, Walkersville, Md.).

Lentivirus-Mediated shRNA Silencing p21 shRNA constructs were from Open Biosystems, Inc. (Huntsville, Ala.). Scramble shRNA construct (Addgene plasmid 1864) was purchased from Addgene, Inc. (Cambridge, Mass.). The p21 RNAi targeting sequences used were as follows: p21 RNAi-1: 5'-cgctctacatcttctgcctta-3' (SEQ ID NO:1) and p21 RNAi-2: 5'-gagcgatggaacttcgacttt-3' (SEQ ID NO:2). Virus production and infection were performed per protocol provided by Addgene.

MTT Assay

MTT cell proliferation assays were performed as follows. Briefly, cells seeded in 12-well plate with or without drug treatment were incubated with 0.5 mg/ml 3-[4, 5-dimethylthiazol-2-yl]-2, 5-diphenyl tetrazolium bromide (MTT) for 1-4 hours. The resulting formazan precipitate was dissolved in isopropanol with 0.04 M HCl. Absorbance was read with a Bio-Rad SmartSpec 3100 at 570 nm with background subtraction read at 690 nm.

Luciferase Assays

Luciferase assays were performed as follows. Briefly, cells transiently transfected with the p21-promoter luciferase construct were treated with or without Lappaol F (50 µM). Twenty-four hours later, luciferase activity of each cell lysate was analyzed using the Luciferase assay system (Thermo Scientific, Rockford, Ill.) with LUMAT LB9507 luminometer (Berthold Technologies, Germany).

Cell Cycle Analysis and Mitotic Index

Cell cycle profile was determined by flow cytometry as follows. For determining the mitotic index, cells treated with or without Lappaol F were stained with 4', 6-diamidino-2-phenylindole (DAPI). The number of mitotic cells was counted under a fluorescence microscope. Over 600 cells were counted in each sample and experiments were repeated at least three times.

Western and Northern Blot Analyses

Western blotting was done by standard protocols. Sources of the antibodies are as follows: antibodies for p21 and GAPDH were from Santa Cruz Biotechnology (Santa Cruz, Calif.); cyclin B1 antibody was from BD bioscience (San Jose, Calif.); p27 antibody was from Cell Signaling Technology (Danvers, Mass.). CDK1 and CDK2 were from Assay Biotechnology (Sunnyvale, Calif.). Northern blot analysis was performed. and a full-length p21 cDNA was used as a probe for detecting the expression of p21 mRNA.

In Vivo Studies

All animal studies were approved and performed according to Animal Care and Use Guidelines of the Animal Ethics Committee at Guangzhou University of Chinese Medicine (Document No. syxk (Yue) 2008-0001). BALB/c nude mice (female, 4-5 weeks old) were first subcutaneously injected with $5 \times 10^6$ of HeLa cells on the back to establish tumor xenografts. Nine-days after tumor cell injection, mice with tumor volume of 90 mm³-290 mm³ were randomized into 3 groups; the average initial tumor volumes in each treatment group of mice were 161.28±23.9 mm³ (for vehicle control), 160.7±17 7 mm³ (for mice treated with Lappaol F 5 mg/kg) and 144.5±20 5 mm³ (for mice treated with Lappaol F 10 mg/kg), respectively. Mice were then treated with Lappaol F (5 mg/kg/d, N=7; or 10 mg/kg/d, N=6) or with equivalent volume of vehicle (5% DMSO plus 5% Tween 80 in 5% glucose solution, 5 mL/kg/day, N=7) by intravenous injection for 15 days. Tumor size was monitored by measuring two perpendicular diameters with a caliper every 4 days. The tumor volume was calculated as volume=length×width²×0.5. Cases of death and body weight in mice were monitored daily. The animal experiments were terminated on day 15 (tumor size exceeded a mean diameter of 20 mm in control animals) by sacrificing mice according to the guidelines. Tumor xenografts were then stripped and weighed. All results were expressed as Mean±standard error of the mean (SEM). Effects of various treatments were analyzed using the ONE-WAY ANOVA analysis and P-values <0.05 were considered statistically significant.

Results

Extraction and Structural Characterization of Lappaol F Isolated from *Arctium lappa* L.

Figure 1:
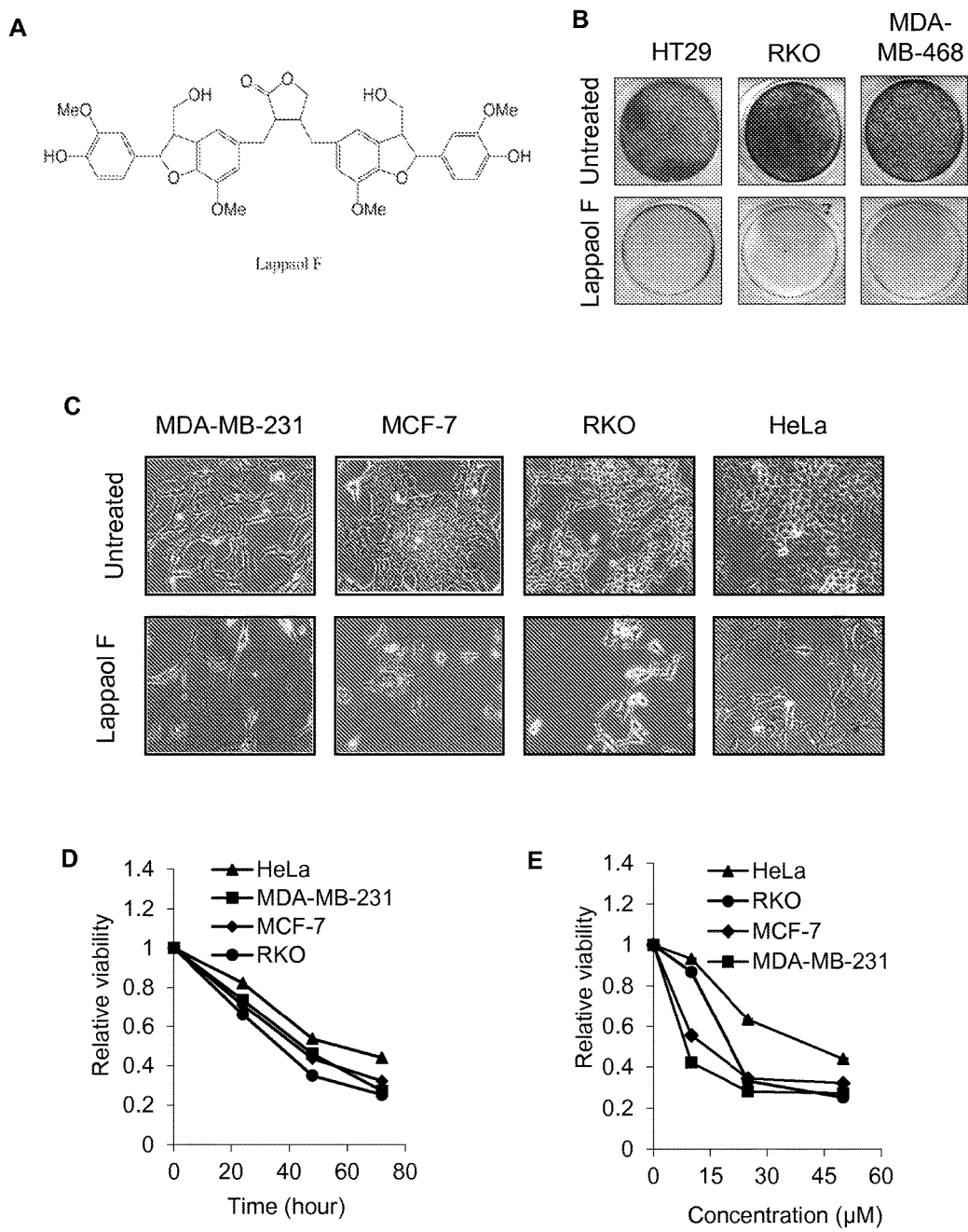
FIG. 1: A. The chemical structure of Lappaol F. B & C. Lappaol F inhibits the growth of tumor cells in various tissue types demonstrated by cell colony formation assay (B) or shown under a phase-contrast microscopy (C). Cells shown were treated with or without Lappaol F (50 µM) for 72 hours. D & E. Results of 3-[4, 5-dimethylthiazol-2-yl]-2, 5-diphenyl tetrazolium bromide (MTT) assays showing Lappaol F inhibits tumor cell growth in time- and dose-dependent manners in different cancer cell lines. F & G. MCF10A non-tumorigenic breast epithelial cells treated with Lappaol F (50 µM) for 3 days (F) or 6 days (G). After treatment, cells were harvested for MTT assays (G) or photographs were taken under a phase contrast microscope (F). H. Results of colony formation assay showing that Lappaol F inhibits colony formation by A549 (lung), HCT116 (colon) and DU145 (prostate) tumor cells. I-N. Results of MTT assays showing Lappaol F suppresses cell growth in leukemia, melanoma and sarcoma cell lines.
Figure 1:
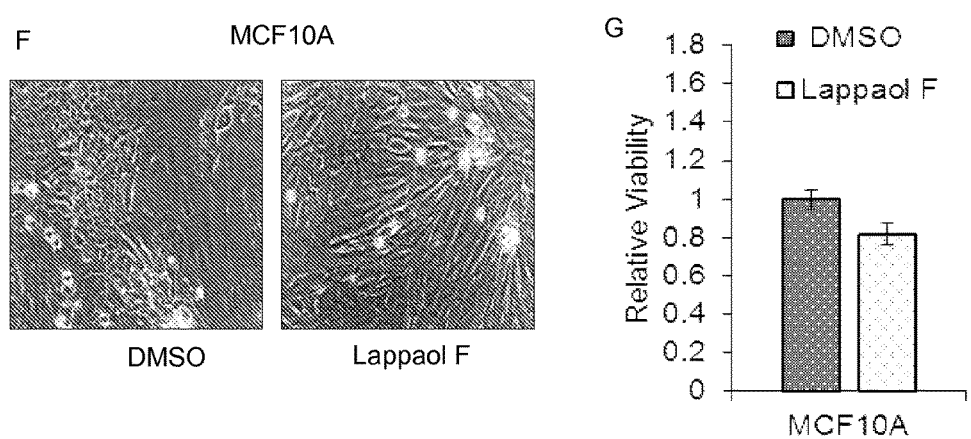
Figure 1:
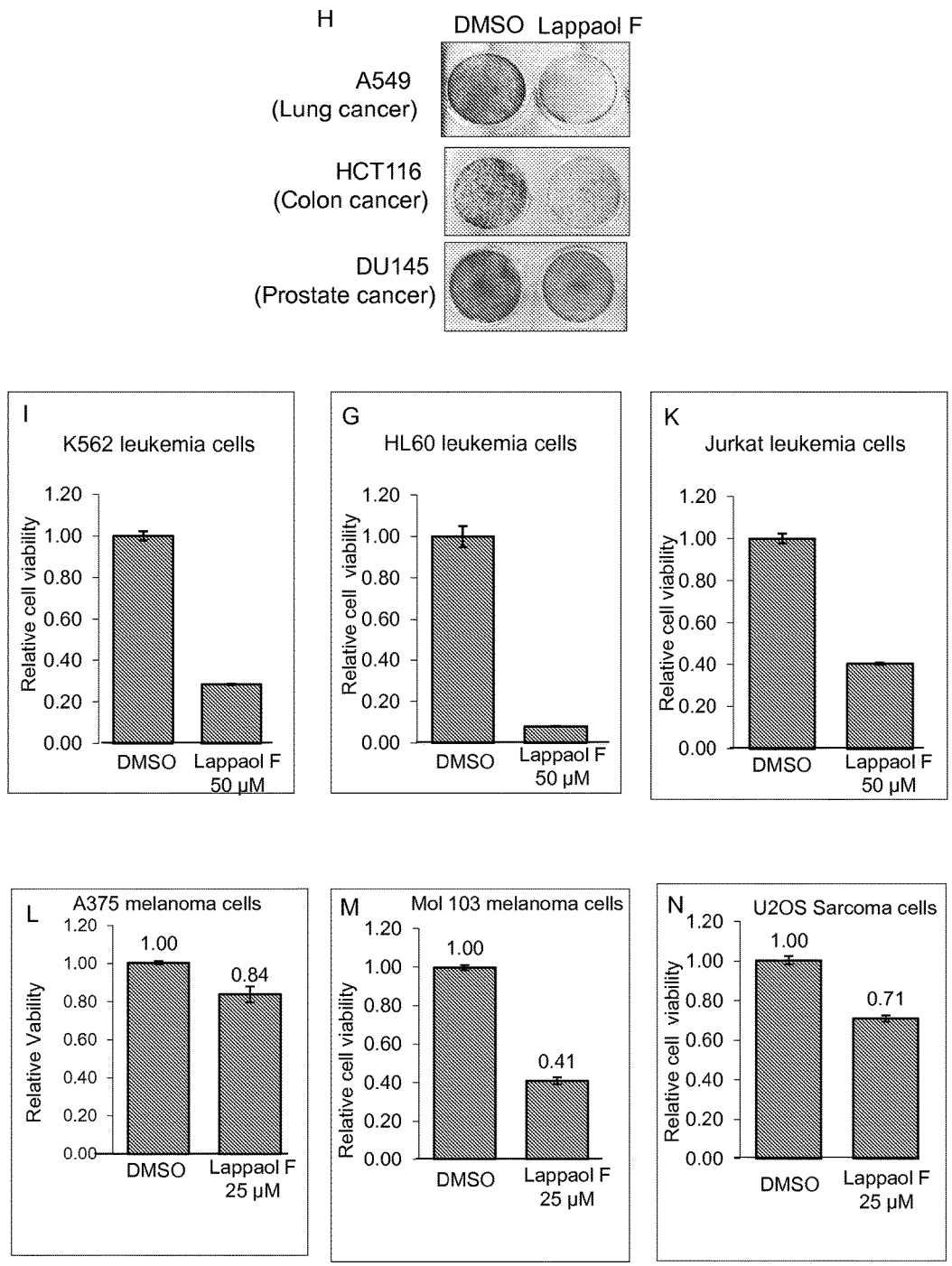

The air-dried and powdered seeds of *Arctium lappa* L. were extracted with methanol (MeOH, 80%) at room temperature. The methanol extract was obtained by removal of methanol in vacuum. The syrup methanol extract was further extracted by petroleum ether, chloroform ($CHCl_3$) and ethyl acetate respectively. The $CHCl_3$ extract (100 g) was then chromatographed repeatedly on silica gels and ODS columns, eluted with $CHCl_3$/MeOH (99:1 to 90:10) and MeOH/$H_2O$ (30:70 to 60:40); after these steps of extraction and purification, a colorless amorphous powder compound, named AL12, was obtained together with twelve other compounds. For structural identification, spectroscopic data for all isolated compounds were measured; UV absorption spectra were run on a TU-1901 UV spectrometer (Purkinje General, China); Electrospray ionization mass spectrometry (ESI-MS) were measured on an API 2000 LC/MS/MS apparatus or a MAT95XP mass spectrometer; $^1H$ and $^{13}C$ nuclear magnetic resonance (NMR) were recorded on a Bruker DRX-400 instrument using tetramethylsilane (™ S) as an internal standard. The chemical structure of AL12 was identified as Lappaol F, based on information of the spectroscopic data, including ESI-MS m/z 749 ([M+Cl]$^-$), UV (MeOH) $\lambda_{max}$ (log ϵ): 232 (4.28), 282 (4.00) nm, and data of $^1H$- and $^{13}C$-NMR (Supplementary information), were complied with those reported. The purity of Lappaol F used in this study was assayed as 99.19% by HPLC. The chemical structure of Lappaol F is shown in FIG. 1A.

The $^1H$ NMR spectra (400 MHz, in $CDCl_3$) of Lappaol F was as follows:

$^1H$-NMR (CDCl3, 400 MHz) δ (ppm): 6.61 (1H, s, H-2), 6.48 (1H, s, H-6), 2.98 (1H, dd, J=14.0, 4.8 Hz, H-7β), 2.84 (1H, dd, J=14.0, 7.2 Hz, H-7α), 2.59 (1H, m, H-8), 6.43 (1H, s, H-2'), 6.53 (1H, s, H-6'), 2.57 (1H, dd, J=13.6, 7.2 Hz, H-7' β), 2.50 (1H, dd, J=14.4, 7.2 Hz, H-7' α), 2.49 (1H, m, H-8'), 4.20 (1H, dd, J=9.2, 6.8 Hz, H-9' β), 3.89 (1H, dd, J=11.2, 5.6 Hz, H-9' α), 6.92 (1H, s, H-2''), 6.82 (1H, d, J=8.0 Hz, H-5''), 6.86 (1H, d, J=2 Hz, H-6''), 5.44 (1H, d, J=7.6 Hz, H-7''), 3.54 (1H, dd, J=12.8, 5.6 Hz, H-8''), 3.88 (1H, m, H-9'' β), 3.87 (1H, m, H-9'' α), 6.92 (1H, s, H-2'''), 6.84 (1H, m, H-5'''), 6.86 (1H, d, J=2.0 Hz, H-6'''), 5.45 (1H, d, J=7.6 Hz, H-7'''), 3.54 (1H, dd, J=12.80, 5.6 Hz, H-8'''), 3.88 (1H, m, H-9'''β), 3.87 (1H, m, H-9'''α), 3.78, 3.82 (3H each, s, 2×OMe), 3.81 (6H, s, 2×OMe).

The $^{13}C$ NMR Spectrum (100 MHz, in $CDCl_3$) of Lappaol F is as follows:

$^{13}$C-NMR (CDCl3, 100 MHz) δ (ppm): 128.4 (C, C-1), 112.8 (CH, C-2), 147.2 (C, C-3), 145.6 (C, C-4), 132.6 (C, C-5), 114.3 (CH, C-6), 34.8 (CH$_2$, C-7), 46.6 (CH, C-8), 178.7 (C, C-9), 128.9 (C, C-1'), 113.2 (CH, C-2'), 147.1 (C, C-3'), 145.6 (C, C-4'), 132.8 (C, C-5'), 114.3 (CH, C-6'), 38.4 (CH$_2$, C-7'), 41.3 (CH, C-8'), 71.3 (CH$_2$, C-9'), 131.0 (C, C-1''), 108.8 (CH, C-2''), 146.7 (C, C-3''), 144.3 (C, C-4''), 116.6 (CH, C-5''), 119.4 (CH, C-6''), 88.0 (CH, C-7''), 53.5 (CH, C-8''), 64.0 (CH$_2$, C-9''), 131.4 (C, C-1'''), 108.8 (CH, C-2'''), 145.7 (C, C-3'''), 144.2 (C, C-4'''), 117.3 (CH, C-5'''), 119.3 (CH, C-6'''), 88.0 (CH, C-7'''), 53.4 (CH, C-8'''), 64.0 (CH$_2$, C-9'''), 56.0 (CH$_3$, C-3'- and C-3''OMe), 56.1 (CH$_3$, C-3''- and C-3'''-OMe).

Lappaol F Exhibits Growth Suppression in Various Tumor Cell Lines.

Through the initial cytotoxic screening assays, we found that Lappaol F exhibited strong growth inhibitory effect against tumor cell lines of different tissue types such as colon (HT29, RKO, HCT116), breast (MCF-7, MDA-MB-231, MDA-MB-468, BT549, Hs578T), lung (A549), cervix (HeLa) and other tissue types (FIGS. 1B & C). We also found that other tumor types such as prostate cancer (DU145), leukemia (K562, HL60 and Jurkat), sarcoma (U2OS) and melanoma (A375, Mol 103) also exhibited growth inhibition following treatment with Lappaol F (FIG. 1H-1N). Lappaol F-mediated cell growth suppression was time- and dose-dependent (FIGS. 1D and E) and the estimated absolute EC$_{50}$ was 13.3, 16.8 and 25.2 µM for MCF-7, MDA-MB-231 and RKO cells respectively. Interestingly, we also found that Lappaol F exhibited minimal cytotoxicity towards MCF10A non-cancerous breast epithelial cells when treated under similar condition (3 days) (FIG. 1F) or with prolonged treatment to six days (FIG. 1G).

Lappaol F Induces $G_1$ and $G_2$ Cell Cycle Arrest and Cell Death.

Figure 2:
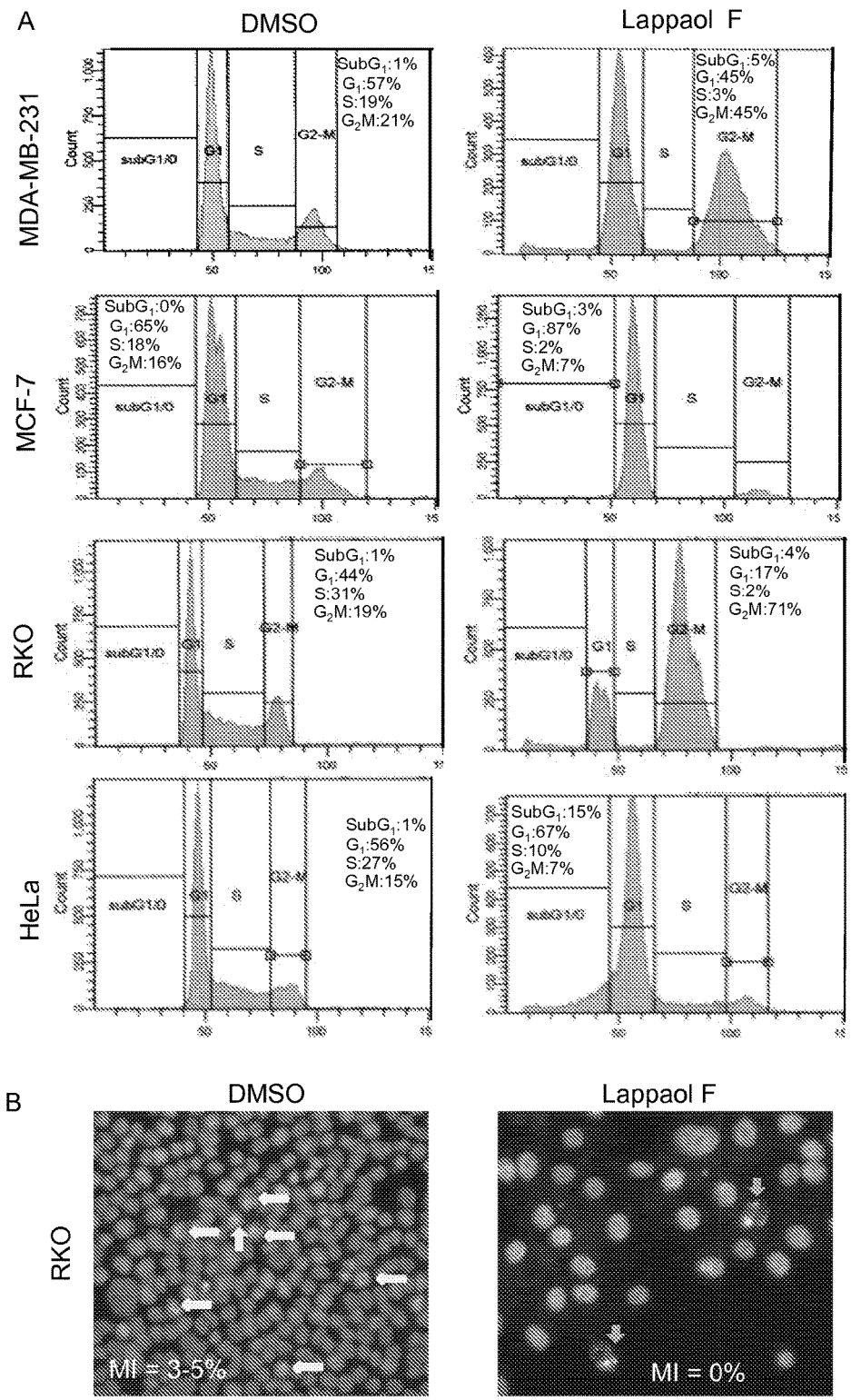
FIG. 2: Lappaol F induces $G_1$ and $G_2$ cell cycle arrest. (A) Flow cytometry cell cycle analyses performed on cells treated with vehicle (DMSO) or Lappaol F (50 µM) for 72 hrs. (B) DAPI staining of RKO cells treated with Lappaol F (50 µM) for 72 hours. The number of mitotic cells over the total cells (mitotic index, MI) is also shown.

We sought to determine the mechanism of action of Lappaol F-mediated cell growth suppression. FIG. 2A shows the results of flow cytometry analysis of Lappaol F-treated and untreated cells. Results of flow cytometry analysis indicated that Lappaol F significantly increased the 2N $G_1$-phase population or the 4N $G_2$- (or M)-phase population in cells (FIG. 2A). It appears that there is some variation in the Lappaol F-elicited response. For example, MCF-7 and HeLa cells were predominantly arrested in 2N $G_1$-phase while MDA-MB-231 and RKO cells were mainly arrested in 4N $G_2$- (or M)-phase (FIG. 2A). Lappaol F not only induced cell cycle arrest, in some cell lines such as HeLa, MDA-MB-231 and RKO, Lappaol F also induced cell death in a subset of cell population. FIG. 2A shows that significant increase (from 1% to 15%) in the sub-2N cell death population (sub-$G_1$) was also observed in Lappaol F-treated HeLa cells. We also noted that as Lappaol F treatment time prolonged to 96 hours the cell death population was further increased (data not shown). To identify whether the 4N-populations were arrested at the $G_2$ or mitotic phase following Lappaol F treatment, mitotic index (MI) was determined FIG. 2B shows that in cell treated with the vehicle (DMSO), the mitotic nuclei were about 3-5% (left panel, arrows). On the other hand, in the Lappaol F-treated cell populations, no mitotic nuclei were observed (FIG. 2B, right panel). These results were reproducible and indicated that the 4N-cell populations represent the $G_2$ phase rather than at the mitotic phase. Furthermore, cell nuclei in Lappaol F-treated cells were bigger as compared to those in the vehicle-treated cells; apoptotic fragmented nuclei were also noted in Lappaol F-treated cells (FIG. 2B, right panel, arrows). These results suggest Lappaol F induced cell cycle arrest at both $G_1$ and $G_2$ phases and it also triggered cell death in subsets of tumor cells.

Lappaol F Affects Cell Cycle Progression by Regulating the Key Cell Cycle Modulators.

We investigated the molecular mechanisms via which Lappaol F induces cell cycle arrest. FIG. 3A-D shows that the expression levels of cyclin-dependent kinase (CDK) inhibitors p21 and p27 were strikingly elevated in Lappaol F-treated cells whereas the levels of CDK2, cyclin B and CDK1 were clearly reduced in different cell lines. It is well-established that CDK2 activity is critical for $G_1$/S transition; whereas p21 and p27 induction prevents $G_1$/S transition; on the other hand, cyclin B/CDK1 activities are required for $G_2$ to M transition and cyclin B/CDK1 are needed for the early onset of mitosis.

Effect of Lappaol F on Apoptotic Signaling.

Figure 4:
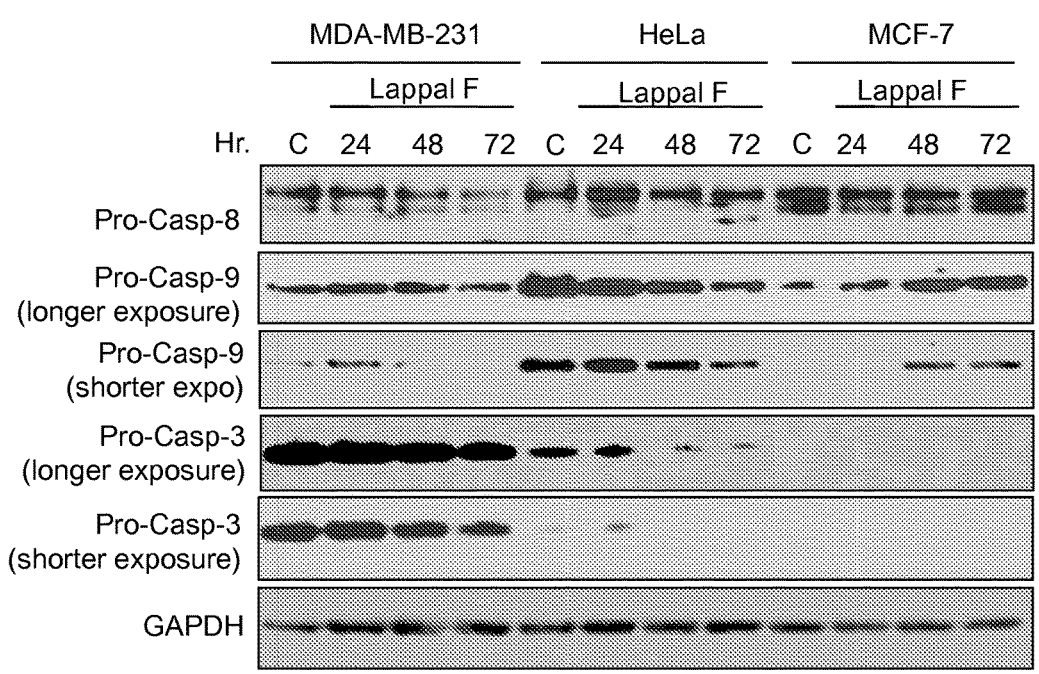
FIG. 4: Effect of Lappaol F on caspase activation. The indicated cells were treated with vehicle (DMSO) or Lappaol F (50 µM) for indicated time. Activation of caspases 8, 9 and 3 (indicated by reduced levels of procaspases) was analyzed by Western blotting using indicated antibodies. "C": vehicle-treated control.

The aforementioned results indicate that Lappaol F not only induced $G_1$ and $G_2$ cell cycle arrest but also triggered cell death in a subset of tumor cell population. Next, we sought to examine the effect of Lappaol F on apoptotic signaling. We found that Lappaol F elicited caspases 9 and 3 activation in HeLa cells (FIG. 4). In MCF-7 cells, however, no clear evidence of caspase activation was noted for caspases 8 and 9. Caspase 3 was not detected in MCF-7 cells due to the gene deletion in the exon 3. In Lappaol F-treated MDA-MB-231 cells, activation of caspases 8, 9 and 3 was observed (FIG. 4). Thus, these results provide biochemical evidence indicating that Lappaol F activates apoptotic signaling in some cell types.

p21 is Crucial for Lappaol F-Mediated $G_2$-Arrest and Cyclin B/CDK1 Down-Regulation.

It is well-established that p21, as a cyclin-dependent kinase inhibitor, plays an essential role in regulation of $G_1$ to S transition. However, the role of p21 at $G_2$-M transition is less studied. Our aforementioned results indicate that p21 induction occurred concurrent with reduction of cyclin B and CDK1, and $G_2$ arrest in Lappaol F-treated RKO and MDA-MB-231 cells (FIG. 3). Previous studies have shown that p21 induction was required for cyclin B down-regulation mediated by histone deacetylase inhibitor butyrate; and p21 was also needed for T-cadherin-mediated $G_2$ arrest. We therefore sought to determine whether p21 induction plays a role on Lappaol F-mediated CDK1/cyclin B suppression and $G_2$ cell cycle arrest. In this context, we first used the p21-knockout cells to investigate whether loss of p21 affects cyclin B and CDK1 expression levels in Lappaol F-treated cells. FIG. 5A shows that cyclin B and CDK1 reduction caused by Lappaol F was significantly abolished in p21-deficient (p21$^{-/-}$) cells (lane 4). We further used the lentivirus-mediated RNAi knockdown approach to study the effect of p21 knockdown on cyclin B and CDK1 regulation. As shown in FIG. 5B, cyclin B and CDK1 reduction observed in scramble RNAi cells (lane 2) after Lappaol F treatment was diminished in p21 knockdown cells (lanes 4 & 6). We further investigated whether p21 depletion had effect on Lappaol F-mediated $G_2$ arrest. As shown in FIGS. 5C and D, depletion of p21 by two different shRNAs targeting different regions of p21 transcript, significantly reduced the proportion of cells arrested in the $G_2$ phase. These results suggest that p21 is critical for Lappaol F-mediated cyclin B/CDK1 suppression and $G_2$ arrest.

Lappaol F Upregulation of p21 Occurs at the Transcriptional Level in a p53-Independent Fashion.

We next investigated whether p21 upregulation by Lappaol F occurs at the transcriptional or the post-transcriptional level. FIG. 6 shows that the levels of p21 mRNA (6A) and protein (6B) were both elevated in Lappaol F-treated cells. These results indicate that Lappaol F-mediated p21 upregulation occurs at the transcriptional level although additional regulation occurring at the post-transcriptional level cannot be ruled out. We then determined whether increased levels of p21 mRNA by Lappaol F occurred due to induced activity at the p21 promoter. Cells introduced with the p21 promoter luciferase constructs were examined for luciferase activity after being treated or untreated with Lappaol F. As seen in FIG. 6C, p21 promoter activity was significantly enhanced in four different cell lines (RKO, MCF-7, Hela, MDA-MB-231) after treatment with Lappaol F. It is of note that while RKO and MCF-7 cells expressing the wild type p53, MDA-MB-231 cells possess a mutant p53 at codon 280 (Arg to Lys), HeLa cells harbor the human papillomavirus that inactivates p53. To further determine whether Lappaol F-mediated p21 upregulation is p53-dependent, RKO p53-proficient ($p53^{+/+}$) and -deficient ($p53^{-/-}$) cells were used to study the promoter activity of p21. As shown in FIG. 6D, Lappaol F caused a 3.5-fold induction of the p21 promoter in $p53^{+/+}$ cells. Interestingly, although the basal levels of p21 was significantly lower in untreated p53-deficient ($p53^{-/-}$) cells as compared to that in untreated p53-proficient ($p53^{+/+}$) cells, Lappaol F was able to upregulate the p21 promoter activity by 8.3-folds in the $p53^{-/-}$ cells (FIG. 6D). Although it is still possible that p53 may contribute to p21 regulation in the p53 proficient cells, our data indicate that Lappaol F-mediated p21 transcriptional induction can occur in a p53-independent manner.

Lappaol F Suppresses Mutant-p53 by Decreasing the Half-Life of Mutant-p53.

It is well-established that mutant-p53 not only loses the function as a tumor suppressor but also gains oncogenic potential that contributes to oncogenic transformation. Next, we sought to determine whether Lappaol F has regulatory effect on the mutant-p53. As shown in FIG. 7, Lappaol F appeared to have no significant influence on the levels of wild-type p53 in MCF-7 cells (FIG. 7A) but significantly reduced the levels of mutant-p53 in MDA-MB-231 cells (B). To further examine the effect of Lappaol F on p53 expression, we examined three additional tumor cell lines that either express the wild-type-p53 (RKO) or the mutant-p53 (MDA-MB-468, T47D). As shown in FIG. 7C, Lappaol F did not significantly affect the expression levels of wild-type-p53 in RKO cells, while the mutant-p53 was strongly inhibited by Lappaol F treatment in MDA-MB-468 and T47D cells. We further examined the possible mechanisms via which Lappaol F down-regulates mutant-p53 levels and to that end investigated the effect of Lappaol F on stability of mutant p53 protein. As shown in FIG. 7D-F, Lappaol F treatment caused a reduction in mutant-p53 protein half-life that was reduced from >8 hours in the untreated cells to ~3 hours in the treated MDA-MB-231 cells (FIGS. 7 D & E). And similar results also were observed in T47D cells (expressing mutant p53) treated with Lappaol F (FIGS. 7 F & G). These results indicate that Lappaol F treatment down-regulates mutant-p53 levels, at least in part, via a reduction in the half-life of the mutant-p53 protein. These results also suggest that Lappaol F appears to cause tumor cell growth inhibition, in part, via its effect on reduction of mutant-p53 levels.

Lappaol F Significantly Down-Regulates the Expression of Several Other Oncogenic Proteins Including c-Myc, MDM2 and HuR.

We examined the effect of Lappaol F on protein expression of c-Myc, MDM2 and HuR. These proteins are commonly overexpressed in human cancers and play important roles in the oncogenic process; and they are also important for maintaining the oncogenic phenotypes of cancer cells. c-Myc and MDM2 are important targets for anticancer drugs development. HuR has also been demonstrated as a determinant of cancer development and plays an important role in tumor aggressiveness in multiple of human cancer types. Our results presented in FIG. 8 indicate that Lappaol F strongly down-regulates these oncoproteins. Our results indicate that Lappaol F, by suppressing multiple oncogenic proteins including above mentioned mutant-p53, c-Myc, MDM2 and HuR and also the cell cycle progression promoters such as CDK1, CDK2, Cyclin B, can effectively suppress cancer cell growth. The ability of Lappaol F on suppression of multi-oncogenic targets was unexpected and is an important advantage of this novel anticancer agent.

Lappaol F Suppresses Tumor Growth in Animals.

We also investigated the effect of Lappaol F on in vivo tumor growth using HeLa cells as xenograft in nude mice. Nine-days after tumor cell inoculations, mice were injected intravenously with vehicle or Lappaol F (5 mg/kg or 10 mg/kg) once daily for 15 days. Our results (FIG. 9) revealed a significant inhibition of tumor growth in mice subjected to Lappaol F treatment. As shown in FIG. 9A, after 15 days of drug treatments, Lappaol F inhibited tumor growth by 54% (5 mg/kg/day, $p<0.001$, N=7) and 64% (10 mg/kg/day, $p<0.001$, N=6) relative to the vehicle-treated cohorts. FIG. 9 also shows that increased Lappaol F dose from 5 mg/kg/day to 10 mg/kg/day further decreased tumor volume and weight Importantly, we did not observe lethality or weight loss in mice that were given Lappaol F (5 mg/kg/day and 10 mg/kg/day) spanning 15-days of treatment (FIG. 9D). These results indicate that the Lappaol F given to the mice was well-tolerated and Lappaol F inhibits tumor growth in vivo. Thus our results, for the first time, indicate that Lappaol F can effectively suppress human tumor (HeLa tumor) grafted on animals and thus provide important information indicating that Lappaol F has a great potential to be developed as anticancer agent for the treatment of human cancers.

While the invention has been described through specific embodiments, those skilled in the art will recognize that routine modifications to the disclosure can be made and such modifications are intend to be within the scope of this disclosure.

The invention claimed is:

1. A method of treatment of cancer comprising administering to an individual in need of treatment an effective amount of isolated and purified Lappaol F in a pharmaceutically acceptable carrier, wherein the Lappaol F is at least 99% pure as determined by HPLC, wherein administration of isolated Lappaol F results in inhibition of tumor growth, and wherein the individual in need of treatment is an individual afflicted with breast cancer, lung cancer, colon cancer, leukemia, melanoma, osteosarcoma, or cervical cancer.

2. The method of claim 1, wherein the Lappaol F is administered by a route that avoids first-pass metabolism.

3. The method of claim 2, wherein the route comprises intravenous, parenteral, intratumoral, intrapulmomnary, intranasal, intracranial or subcutaneous administration.

4. The method of claim 3, wherein the administration is performed prior to, concurrently with, or subsequent to chemotherapy, surgical treatment, or radiation treatment of the individual.

5. The method of claim 1, wherein the individual has not responded to treatment with a chemotherapeutic agent.

6. The method of claim 1, wherein the cancer cells exhibit a mutant-p53 or a wild type p53.

7. The method of claim 1, wherein the cancer cells are present in a tumor.

8. The method of claim 5, wherein the cancer cells exhibit a mutant p53.

9. The method of claim 5, wherein the cancer cells exhibit a wild type p53.

10. The method of claim 1, wherein the Lappaol F is administered with at least one additional chemotherapeutic agent.

11. The method of claim 10, wherein the at least one additional chemotherapeutic agent is selected from the group consisting of Cisplatin, Doxorubicin, Etoposide, Bleomycin, Cetuximab, Trastuzumab, a *vinca* alkaloid, a taxane, colchicine, and combinations thereof.

12. The method of claim 1, wherein the individual in need of treatment has been diagnosed with a tumor.

13. The method of claim 1, wherein Lappaol F is administered at a dose of from 1 mg/kg/day to 10 mg/kg/day.

14. The method of claim 13, wherein Lappaol F is administered for from 1 day to 30 days.

* * * * *

UNITED STATES PATENT AND TRADEMARK OFFICE
CERTIFICATE OF CORRECTION

PATENT NO.         : 9,895,345 B2
APPLICATION NO.    : 14/889534
DATED              : February 20, 2018
INVENTOR(S)        : Ying Huang Page 1 of 1

It is certified that error appears in the above-identified patent and that said Letters Patent is hereby corrected as shown below:

In the Claims

Column 13, Line 32, in Claim 3, "intrapulmomnary" should read:
--intrapulmonary--.

Signed and Sealed this
Sixteenth Day of October, 2018

Andrei Iancu
*Director of the United States Patent and Trademark Office*